United States Patent
Diederich et al.

Patent Number: 5,456,672
Date of Patent: Oct. 10, 1995

[54] SYRINGE-LIKE DEVICE FOR THE DOSING OF LIQUIDS OR PASTES

[75] Inventors: Reiner Diederich, Wesseling; Alfred von Schuckmann, Kevelaer, both of Germany

[73] Assignee: Bayer Aktiengesellschaft, Leverkusen, Germany

[21] Appl. No.: 161,357

[22] Filed: Dec. 2, 1993

Related U.S. Application Data

[63] Continuation of Ser. No. 896,259, Jun. 10, 1992, abandoned.

[30] Foreign Application Priority Data

Jun. 20, 1991 [DE] Germany ............... 9107574 U

[51] Int. Cl.⁶ ............... A61M 5/315
[52] U.S. Cl. ............... 604/226; 604/89; 433/80
[58] Field of Search ............... 604/226, 82, 83, 604/85, 236, 237, 207, 208, 216, 218, 89, 90, 212, 183, 184, 213, 215, 232, 235; 433/80, 89

[56] References Cited

U.S. PATENT DOCUMENTS

| | | | |
|---|---|---|---|
| 2,029,734 | 7/1933 | Meitzler | 433/80 |
| 2,413,303 | 12/1946 | Folkman | 604/135 |
| 3,340,369 | 9/1967 | Bane . | |
| 3,548,824 | 12/1970 | Carr | 604/218 |
| 3,827,601 | 8/1974 | Magrath et al. . | |
| 4,060,082 | 11/1977 | Lindberg et al. | 604/89 |
| 4,254,769 | 3/1981 | Sneider | 604/249 |
| 5,181,909 | 1/1993 | McFarlane | 604/52 |

FOREIGN PATENT DOCUMENTS

| | | |
|---|---|---|
| 0478956 | 10/1973 | Australia . |
| 2342744 | 3/1977 | France . |
| 2106338 | 10/1971 | Germany . |
| 3527066 | 7/1985 | Germany . |

*Primary Examiner*—C. Fred Rosenbaum
*Assistant Examiner*—V. Alexander
*Attorney, Agent, or Firm*—Sprung Horn Kramer & Woods

[57] ABSTRACT

A liquid can be dosed advantageously using a syringe-like device, from a container fitted thereon, by means of a plunger mounted displaceably in a dosing chamber, this dosing chamber being connected to the container via a channnel passing through this plunger, a valve and a channel arranged together with the plunger in a connection tube.

5 Claims, 1 Drawing Sheet

U.S. Patent  Oct. 10, 1995  5,456,672
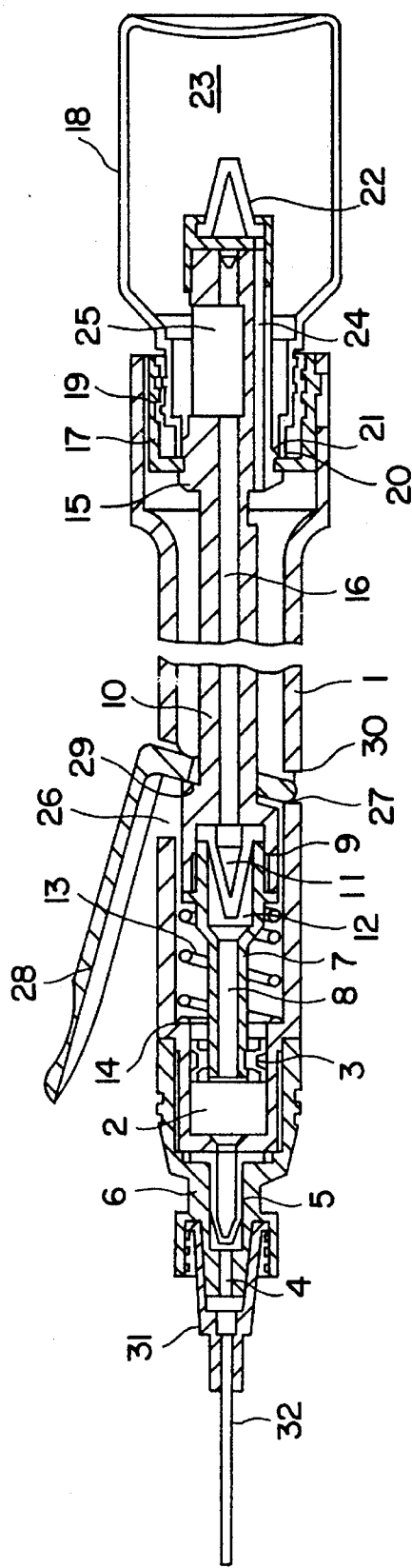
FIG. 1
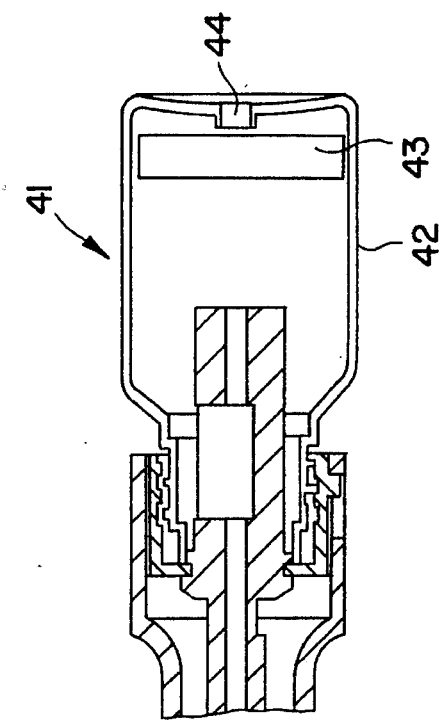
FIG. 3
FIG. 2

5,456,672

SYRINGE-LIKE DEVICE FOR THE DOSING OF LIQUIDS OR PASTES

This application is a continuation of application Ser. No. 07/896,259, filed Jun. 10, 1992, now abandoned.

BACKGROUND OF THE INVENTION

The invention relates to a syringe-like device for the dosing of liquids or pastes, consisting of a housing with a plunger, a storage chamber and an outlet opening at the end of the housing.

In the medical field, particularly in the dental field, syringe-like devices, also called applicators, are needed for the dosing of liquids or thin pastes.

In known devices, the liquid must be drawn in by means of the plunger, in order to fill the storage chamber situated inside the device. This handling is awkward, liquid can be contaminated or spilled, or the container knocked over. In addition, the container cannot be emptied completely.

SUMMARY OF THE INVENTION

The object of the present invention is to improve the device of the type mentioned at the outset in such a way that the filling and the handling are simpler and the container can be emptied completely.

This object is achieved by virtue of the fact that a valve is arranged upstream of the outlet opening; that a dosing chamber with a plunger guided therein is arranged upstream of the valve, a channel leading through the plunger and its adjoining shaft; that the end of this shaft is held in a leakproof manner in a connection tube guided displaceably in the housing, a valve being arranged between the channel of the shaft and the channel of the connection tube; that at the end of the connection tube there is a holding arrangement for a storage chamber which can be fitted in a leakproof manner in the form of an exchangeable container, and that the connection tube can be moved by means of a lever in the direction of the outlet opening counter to a return spring bearing on the housing.

This design of the device has the advantage that the storage containers containing the liquid can be secured directly on the device, so that their contents, without any special manipulations being required, can be used up gradually, and indeed completely. The containers can be connected in a leakproof manner to the connection tube, for example by means of a screw thread, this screw thread serving previously as a holding arrangement for the closure cap of the container. As soon as the container is fitted, the contents are protected. Spillage of the liquid can only take place while the container is being fitted. However, it is also of importance that the container can be emptied completely. The device can be produced and assembled entirely from plastic components, which have been made by injection-moulding. The valve consists most simply of a plane sealing disc, which closes the outlet opening of the channel of the connection tube when the partial vacuum is developed.

According to a first particular embodiment, an aeration valve connected to the atmosphere is arranged at the end of the connection tube projecting into the container.

In this way, the partial vacuum building up in the container during dosing is compensated by air being drawn in. A rubber-elastic valve or a spring-loaded ball valve is suitable.

However, it is also possible to give the container a bellows formation or to design it as a cartridge with a draw plunger.

These embodiments are particularly advantageous when the liquid is not to come into contact with air. The bellows or the draw plunger then ensures that the partial vacuum is offset by volume compensation.

BRIEF DESCRIPTION OF THE DRAWINGS

The new device is described in greater detail hereinbelow and is illustrated purely diagrammatically in the drawing, in which:

FIG. 1 shows the device in longitudinal section, and

FIGS. 2 and 3 show modified embodiments of the container of the device.

DESCRIPTION OF THE PREFERRED EMBODIMENTS

In FIG. 1 the device consists of a housing 1, in which a plunger 3 is guided in a dosing chamber 2. Arranged upstream of an outlet opening 4 is a valve 5 which is made of rubber-elastic material and which is clamped between a head piece 6 and the housing 1. The plunger 3 merges into a shaft 7. Both have an axially arranged channel 8 passing through them. The shaft 7 is screwed in a leakproof manner into a recess 9 of a connection tube 10 mounted displaceably in the housing 1. Arranged in that part of the recess 9 remaining free is a valve 11, which likewise consists of rubber-elastic material. It projects into a widened area 12 of the channel 8 in the shaft 7. The shaft 7 is surrounded by a return spring 13, which on the one hand bears on a shoulder 14 of the housing 1 and on the other hand pushes against the connection tube 10. The end 15 of the connection tube 10, likewise having a channel 16 passing through it, has a holding arrangement 17 in which a container 18 is held by means of a thread connection 19. In order to ensure that the edge 20 of the container 18 is leakproof, the connection tube 10 at this position has a cone attachment 21. In addition, the end 15 of the connection tube 10 is further provided with an aeration valve 22, which is made of rubber-elastic material and which can connect the interior 23 of the container 18 to the atmosphere via a channel 24. A recess 25 ensures the flow from the interior 23 into the channel 16. The housing 1 is provided with recesses 26 and 27, which lie opposite one another and in which a lever 28 engages. The latter bears against shoulders 29 and 30 of the connection tube 10, the position of the recesses 26, 27 and of the shoulders 29, 30 being adapted in conjunction with the geometry of the lever 28 in such a way that, when the lever 28 is actuated, the connection tube 10 is displaced in the direction of the outlet opening 4 counter to the tension force of the return spring 13. An adapter 31 with a channel 32 is attached on the outside to the head piece 6.

In FIG. 2 the container 51 is designed in bellows formation and consists of an elastic synthetic material.

In FIG. 3 the container 41 consists of a cartridge 42 with a draw plunger 43. Atmospheric pressure is maintained on one side of the plunger 43 by the airhole 44.

The operating principle of the new device according to FIG. 1 is as follows: First, the container 18 is arranged on the holding arrangement 17 by means of its closure cap being removed and the thread connection 19 then being made, with the housing 1 held facing up. The device is then held facing down, so that the liquid flows through the channels 16 and 8 into the dosing chamber 2. The valve 5 is closed by virtue of its elasticity. By actuating the lever 28, the connection tube 10 and plunger 3 are displaced in the direction of the outlet opening 4, as a result of which the valve 11 is closed by the partial vacuum being developed and the valve 5 is stretched by the pressure and opened. A displaced volume of liquid corresponding to the advance of the plunger is now dosed. When the lever 28 is released, the return spring 13 pushes the connection tube 10 and plunger 3 back into their initial positions. In so doing, the valve 5 closes, and the valve 11 opens as a result of the partial vacuum developing in the channel 8 and in the dosing chamber 2, so that liquid is again drawn into the chamber 2. A partial vacuum also develops in the container 18, as a result of which the elastic aeration valve 22 opens and draws air from the atmosphere into the interior 23 of the container 18 via the channel 24. The device is now ready for the next dosing procedure. If the container 18 is empty, it is replaced by a new one.

The operating principle of the device according to the modified embodiment in FIG. 2 is as described above, but with the difference that, because there is no possibility of aeration, the bellows of the container 51 takes over the volume compensation, as a result of which the partial vacuum is reduced.

Similarly, in the modified embodiment of FIG. 3, the volume compensation is effected by the plunger vacuum on the left side of the plunger 43 (in the sense of the drawing) which causes the plunger to move toward the left.

There has thus been shown and described a novel syringe-like device for the dosing of liquids or pastes which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. Syringe-like device for the dosing of liquids or pastes, comprising an elongate housing having a central axis and an outlet opening at one end, a dosing chamber a multi-dose storage chamber, and a liquid or paste within the storage chamber or dosing chamber, said dosing chamber being positioned between said outlet opening and said storage chamber and cyclically in communication with said outlet opening or said storage chamber, and a plunger disposed coaxially in the dosing chamber and operative to move longitudinally therein in the direction of said axis and having first and second check valves, the first check valve being disposed between the dosing chamber and the outlet opening, said first check valve opening under the pressure of the liquid or paste when the plunger moves towards the outlet opening; said plunger including a piston member and an adjoining shaft, a channel leading through the piston member and its adjoining shaft; the end of said shaft being held in a leakproof manner in a connection tube which has a channel therein and being guided displaceably in the housing; the second check valve being disposed between the channel of the shaft and the channel of the connection tube; at the end of the connection tube a holding arrangement for the multi-dose storage chamber which can be fitted in a leakproof manner in the form of an exchangeable container; a lever and a return spring bearing on the housing, said lever operatively connected to the connection tube and the plunger so that they can be moved by said lever in the direction of the outlet opening counter to the return spring bearing on the housing; the second check valve opening under the partial vacuum developed in the dosing chamber when the return spring is allowed to move the plunger in a direction away from the outlet opening, wherein movement of the lever in one direction causes said liquid or paste present in the dosing chamber to be discharged through said outlet opening, and movement of the lever in the opposite direction causes said liquid or paste contained in the storage chamber to be transferred to the dosing chamber repeated movements of said lever serving repeatedly to transfer said liquid or paste from said storage chamber to said dosing chamber and then to discharge said liquid or paste from said dosing chamber through said outlet opening a multitude of times.

2. Syringe-like device according to claim 1, further including an aeration valve at the end of the connection tube projecting into the container, said aeration valve being connected between the container and the atmosphere.

3. Syringe-like device according to claim 1, wherein the container is designed in a bellows formation.

4. Syringe-like device according to claim 1, wherein the container consists of a cartridge with a draw plunger.

5. Syringe-like device according to claim 1, wherein said first and second check valves are rubber-elastic valves.

* * * * *